(12) United States Patent
McQuirter, Sr.

(10) Patent No.: US 11,439,840 B2
(45) Date of Patent: Sep. 13, 2022

(54) FAR ULTRAVIOLET LIGHT APPLICATION DEVICE

(71) Applicant: Joseph McQuirter, Sr., Los Angeles, CA (US)

(72) Inventor: Joseph McQuirter, Sr., Los Angeles, CA (US)

( * ) Notice: Subject to any disclaimer, the term of this patent is extended or adjusted under 35 U.S.C. 154(b) by 0 days.

(21) Appl. No.: 17/154,069

(22) Filed: Jan. 21, 2021

(65) Prior Publication Data

US 2022/0226669 A1    Jul. 21, 2022

(51) Int. Cl.
| | |
|---|---|
| *A61N 5/06* | (2006.01) |
| *G02B 6/10* | (2006.01) |
| *F21V 8/00* | (2006.01) |
| *A61B 13/00* | (2006.01) |
| *A61M 1/00* | (2006.01) |

(52) U.S. Cl.
CPC ......... *A61N 5/0624* (2013.01); *G02B 6/0006* (2013.01); *G02B 6/0008* (2013.01); *G02B 6/102* (2013.01); *A61B 13/00* (2013.01); *A61M 1/84* (2021.05); *A61N 2005/063* (2013.01); *A61N 2005/0606* (2013.01); *A61N 2005/0643* (2013.01); *A61N 2005/0661* (2013.01)

(58) Field of Classification Search
CPC .......... A61N 5/0624; A61N 2005/0661; G02B 6/102
USPC ......................................................... 607/88
See application file for complete search history.

(56) References Cited

U.S. PATENT DOCUMENTS

| | | |
|---|---|---|
| 7,201,767 B2 | 4/2007 | Bhullar |
| 8,258,603 B2 | 9/2012 | Watanabe |
| 9,095,704 B2 | 8/2015 | McGuire |
| D787,084 S | 5/2017 | Sarchese |
| 10,369,379 B2 | 8/2019 | Randers-Pehrson |
| 2009/0143842 A1 | 6/2009 | Cumbie |
| 2009/0314308 A1 | 12/2009 | Kim |
| 2017/0119915 A1* | 5/2017 | Lin ................. A61M 25/01 |
| 2019/0168023 A1* | 6/2019 | Eltorai ............. A61M 1/3661 |

FOREIGN PATENT DOCUMENTS

WO    WO2012122210    9/2012

\* cited by examiner

*Primary Examiner* — Lynsey C Eiseman
*Assistant Examiner* — Jessica L Mullins (57) ABSTRACT

A far ultraviolet light application device for killing pathogens on tissue and proximate thereto includes a tube that is to be utilized in a medical procedure. A first fiberoptic cable is engaged to a wall of the tube so that a first end of the first fiberoptic cable is positioned proximate to a first terminus of the tube. The first fiberoptic cable has a second end operationally engaged an ultraviolet C light emitter so that ultraviolet C light is emitted proximate to the first terminus of the tube. The first fiberoptic cable directs the ultraviolet C light from the ultraviolet C light emitter so that the ultraviolet C light impinges upon tissue and pathogens proximate to the first terminus of the tube to inactivate the pathogens.

8 Claims, 9 Drawing Sheets

FAR ULTRAVIOLET LIGHT APPLICATION DEVICE

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

The disclosure relates to light application devices and more particularly pertains to a new light application device for killing pathogens on tissue and proximate thereto. The present invention discloses a device comprising a first fiber optic cable for directing UV light onto tissue being manipulated as part of a medical procedure, or such a device also incorporating a suction tube or a second fiber optic cable for directing visible light onto the tissue.

(2) Description of Related Art Including Information Disclosed Under 37 CFR 1.97 and 1.98

The prior art relates to light application devices, which may comprise UV light or far UV light devices for destroying pathogens on tissue without harming human cells. What is lacking in the prior art is a device comprising a first fiber optic cable for directing UV light onto tissue being manipulated as part of a medical procedure, or such a device also incorporating a suction tube or a second fiber optic cable for directing visible light onto the tissue.

BRIEF SUMMARY OF THE INVENTION

An embodiment of the disclosure meets the needs presented above by generally comprising a tube, which is configured to be utilized in a medical procedure, such as a tube intended for suctioning, fluid flow, or endoscopy. A first fiberoptic cable is engaged to a wall of the tube so that a first end of the first fiberoptic cable is positioned proximate to a first terminus of the tube. The first fiberoptic cable has a second end configured to operationally engage an ultraviolet C light emitter so that ultraviolet C light is emitted proximate to the first terminus of the tube. The first fiberoptic cable is configured to direct the ultraviolet C light from the ultraviolet C light emitter so that the ultraviolet C light impinges upon tissue and pathogens proximate to the first terminus of the tube to inactivate the pathogens.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

With reference now to the drawings, and in particular to FIGS. 1 through 9 thereof, a new light application device embodying the principles and concepts of an embodiment of the disclosure and generally designated by the reference numeral 10 will be described.

Figure 1:
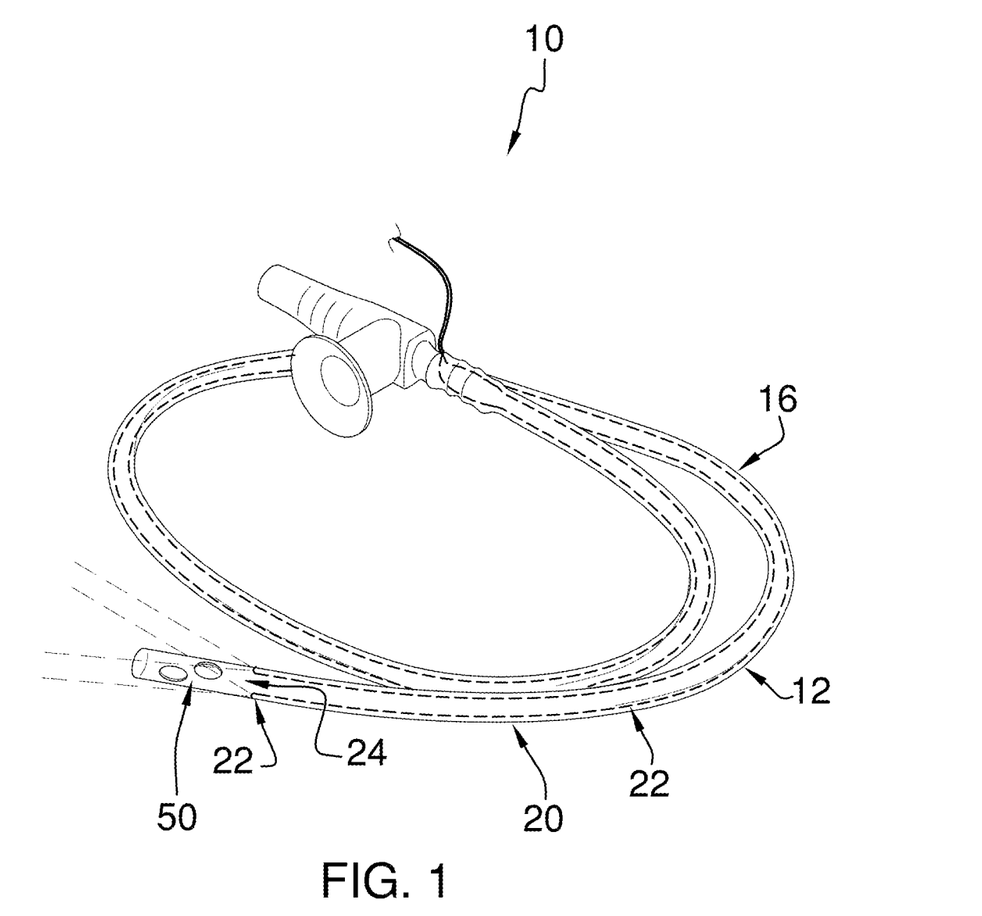
FIG. 1 is an isometric perspective view of a far ultraviolet light application device according to an embodiment of the disclosure.
Figure 2:
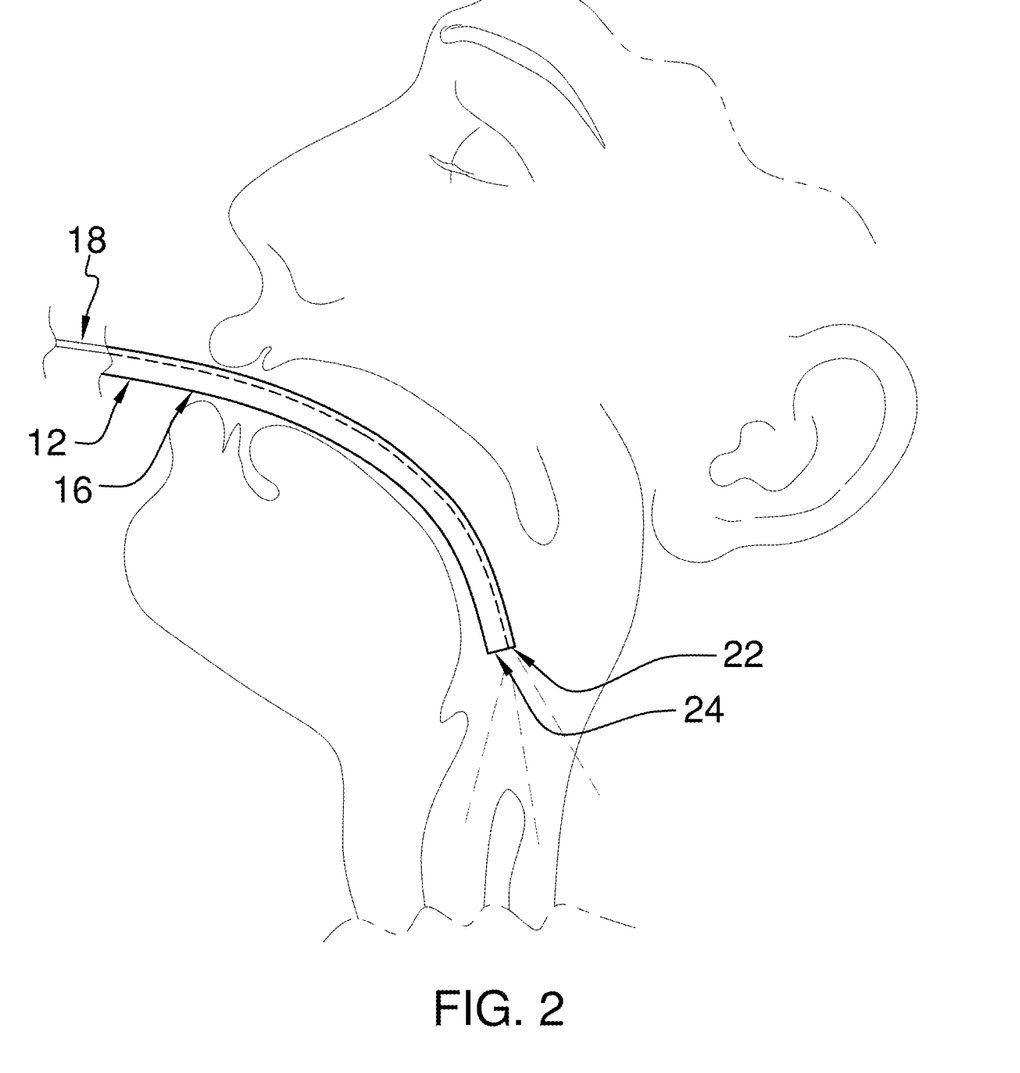
FIG. 2 is an in-use view of an embodiment of the disclosure.
Figure 3:
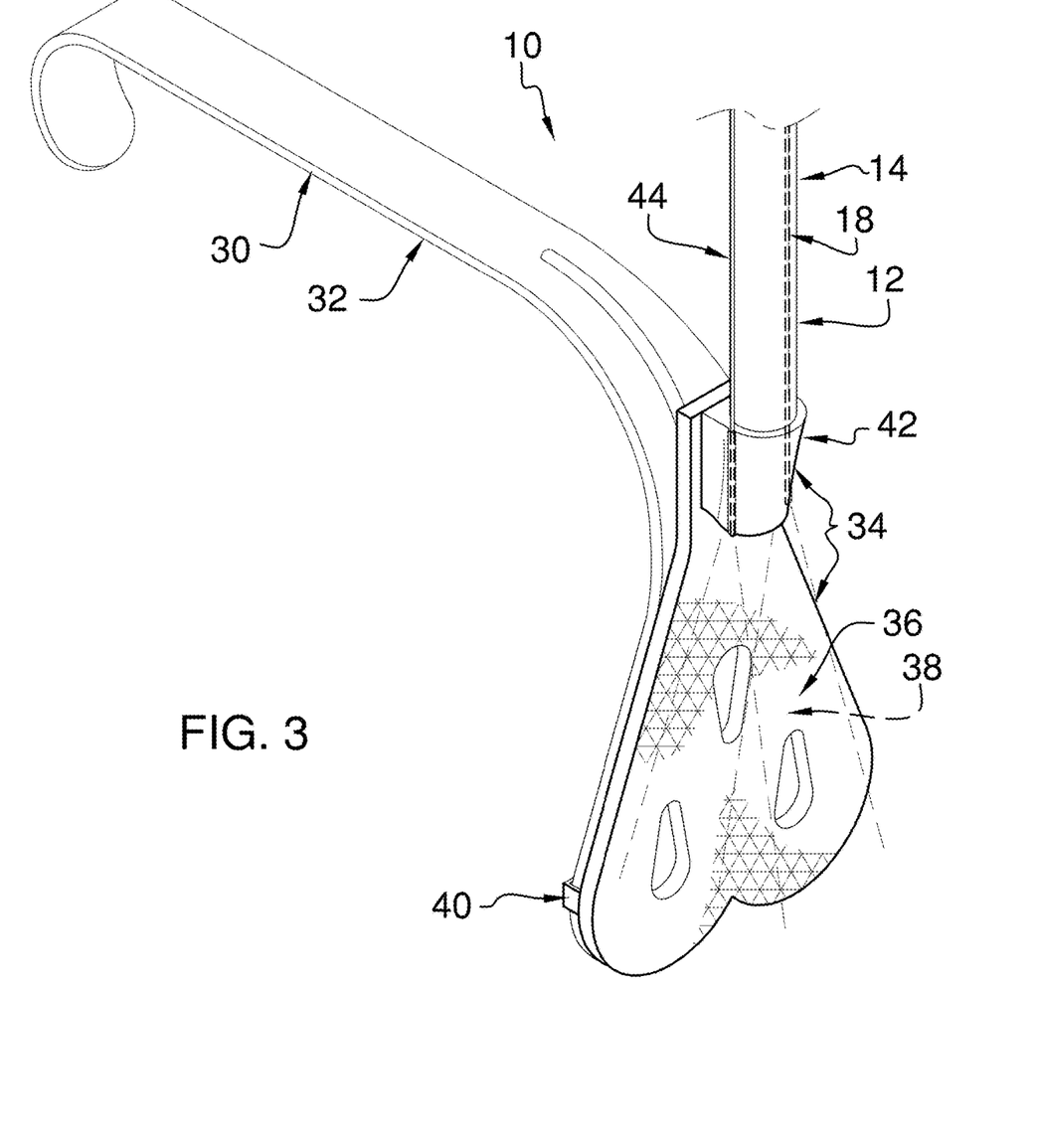
FIG. 3 is an isometric perspective view of an embodiment of the disclosure.
Figure 4:
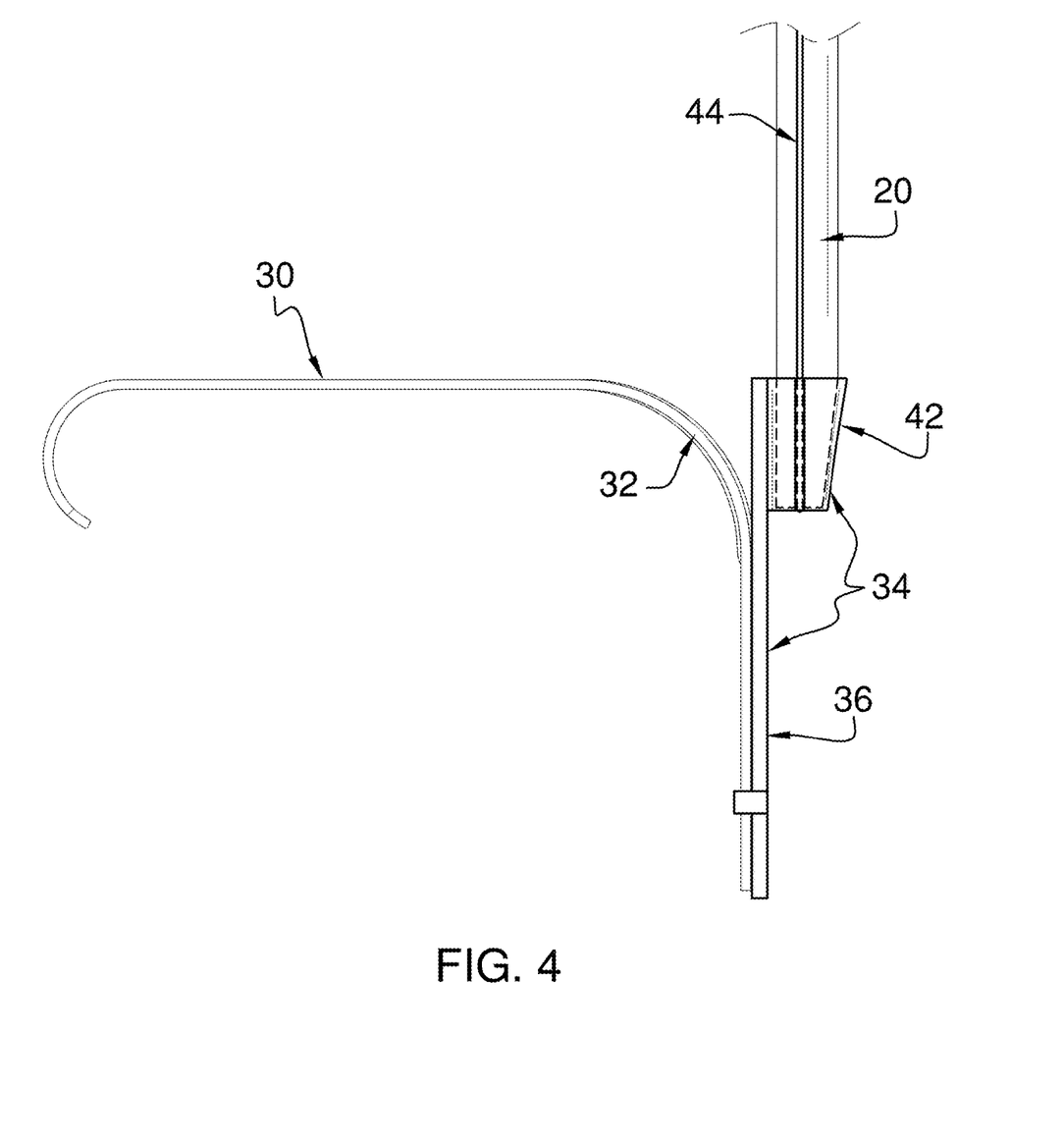
FIG. 4 is a side view of an embodiment of the disclosure.
Figure 5:
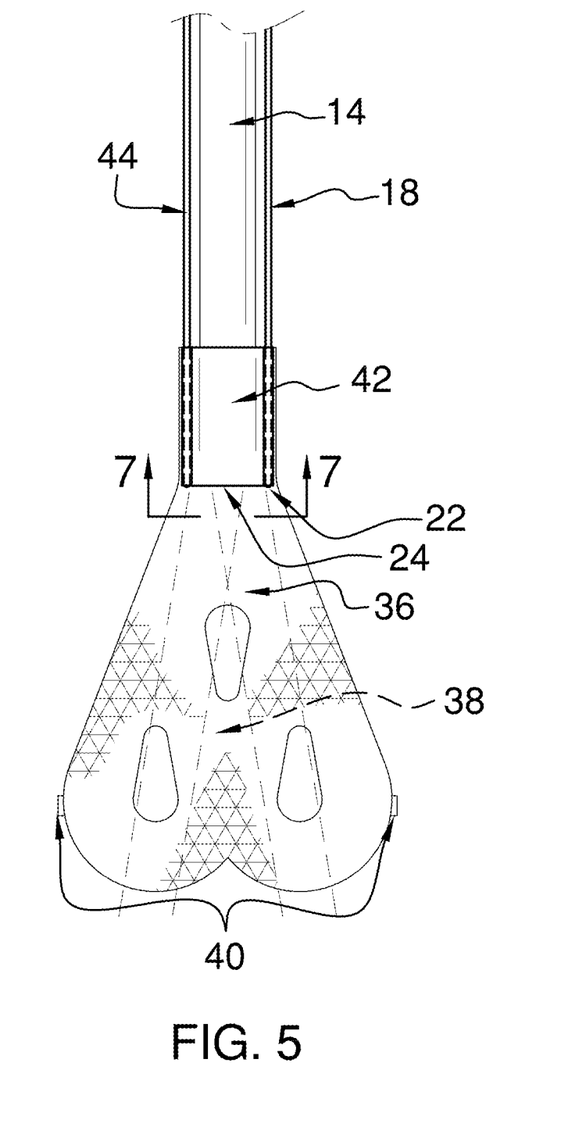
FIG. 5 is a front view of an embodiment of the disclosure.
Figure 6:
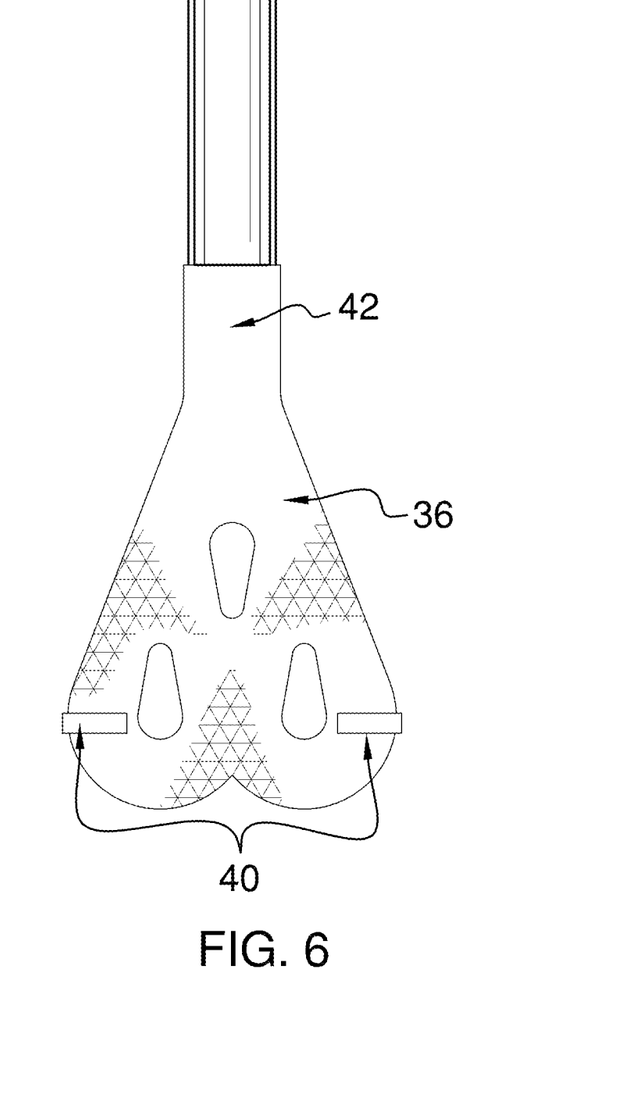
FIG. 6 is a back view of an embodiment of the disclosure.
Figure 7:
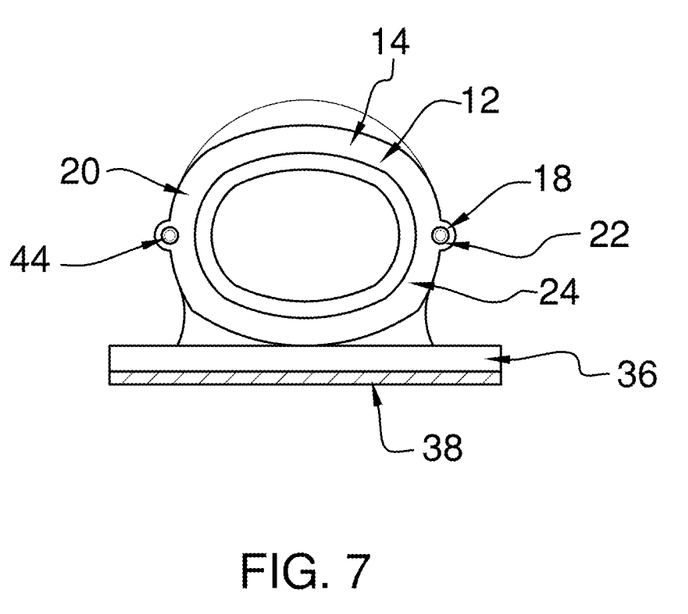
FIG. 7 is a bottom view of an embodiment of the disclosure.
Figure 8:
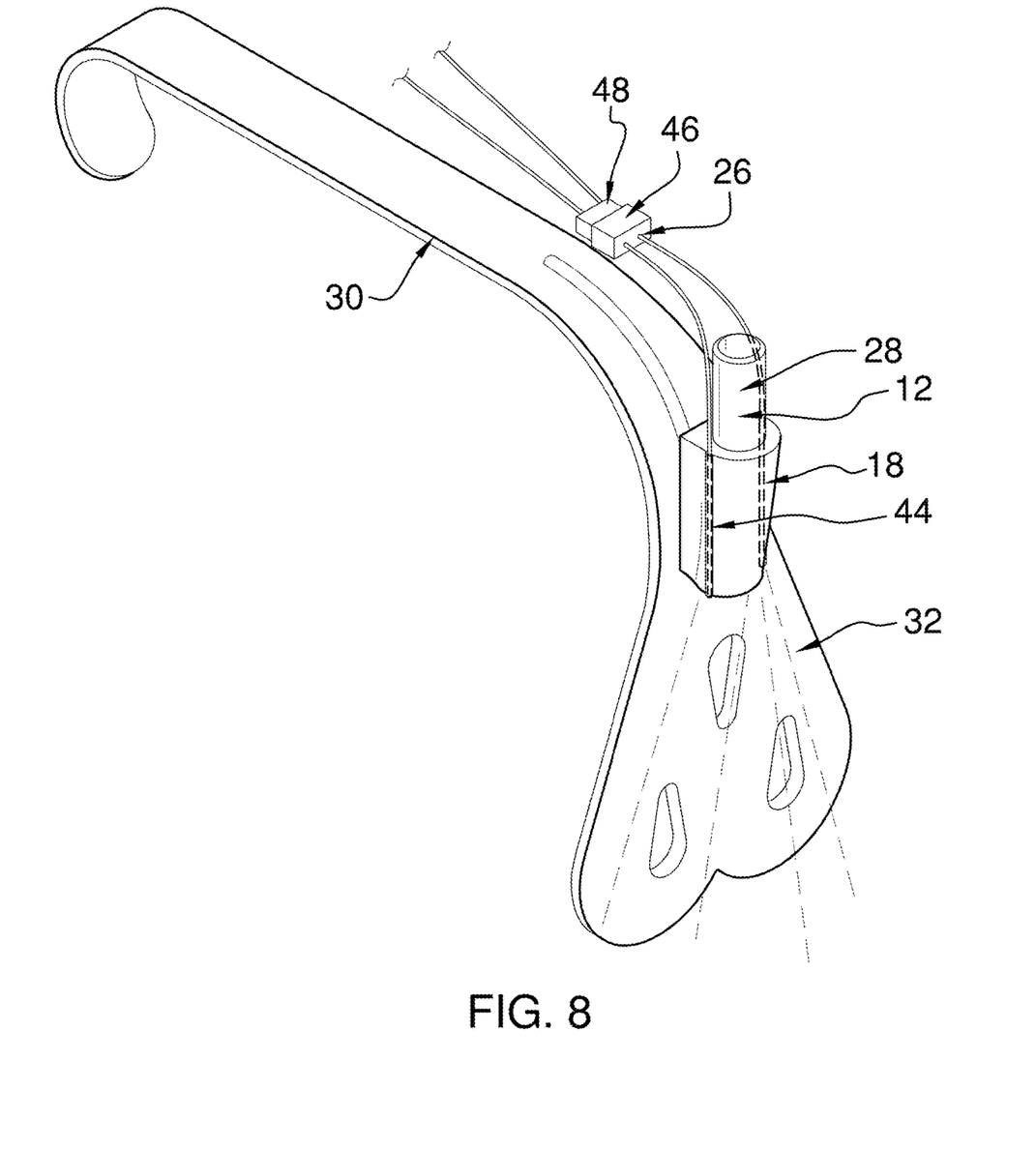
FIG. 8 is an isometric perspective view of an embodiment of the disclosure.
Figure 9:
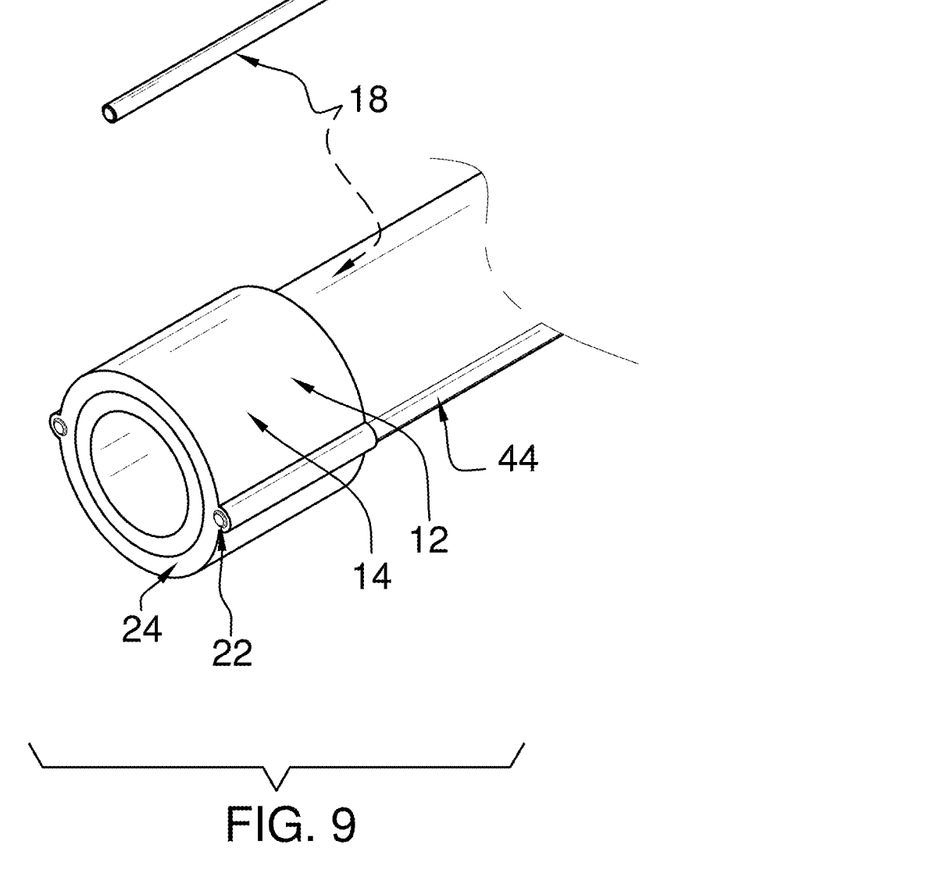
FIG. 9 is a detail view of an embodiment of the disclosure.

As best illustrated in FIGS. 1 through 9, the far ultraviolet light application device 10 generally comprises a tube 12, which is configured to be utilized in a medical procedure. The tube 12 may be configured for suctioning, fluid flow, or endoscopy. For example, the tube 12 may comprise a suction tube 14, as shown in FIGS. 3 and 9, a suction catheter 16, as shown in FIG. 2, an endoscopy tube (not shown), an intravenous tube (not shown), a shunt (not shown), a dialysis catheter (not shown), and the like. The suction catheter 16 may have a perforated bladder 50 engaged to a first terminus thereof.

A first fiberoptic cable 18 is engaged to a wall 20 of the tube 12 so that a first end 22 of the first fiberoptic cable 18 is positioned proximate to the first terminus 24 of the tube 12. The first fiberoptic cable 18 has a second end 26 configured to be operationally engaged to an ultraviolet C light emitter (not shown) so that ultraviolet C light is emitted proximate to the first terminus 24 of the tube 12. The first fiberoptic cable 18 is configured to direct the ultraviolet C light from the ultraviolet C light emitter so that the ultraviolet C light impinges upon tissue and pathogens proximate to the first terminus 24 of the tube 12 to inactivate the pathogens. The ultraviolet C light emitter emits at 222 nanometers so that the ultraviolet C light is nondamaging to mammalian tissue.

In one embodiment, as shown in FIG. 8, the tube 12 comprises a pipe 28, which is integral to a medical instrument 30. The pipe 28 is circumferentially complementary to a prior art suction tube lacking the first fiberoptic cable 18. The pipe 28 is configured to selectively engage the prior art suction tube so that the prior art suction tube is removably and operationally engaged to the pipe 28. The prior art suction tube is configured to remove debris, droplets, particles, and aerosols generated during the medical procedure performed using the medical instrument 30 and thus serves to reduce a probability of transfer of pathogens to a surrounding environment and persons therein, relative to a prior art medical instrument lacking the pipe 28.

The medical instrument 30 may comprise an examination instrument, such as a tongue retractor 32, as shown in FIG. 8, a surgical instrument, a dental instrument, or a veterinary instrument. For example, the medical instrument 30 may comprise a retractor (not shown), a probe (not shown), a clamp (not shown), a forceps (not shown), and the like.

In another embodiment, as shown in FIGS. 3-7, the device 10 comprises an adapter 34, which is selectively engageable to the tube 12. The adapter 34 is configured to selectively engage a medical instrument 30 so that the tube 12 is removably engaged to the medical instrument 30. The adapter 34 may comprise a plate 36, which is shaped complementarily to a portion 38 of the medical instrument 30. A set of clips 40 is engaged to the plate 36 and is configured to engage the medical instrument 30 so that the adapter 34 is removably engaged thereto with the plate 36 overlying the portion 38 of the medical instrument 30. A receptacle 42 engaged to the plate 36 is complementary to the tube 12. The receptacle 42 is positioned for insertion of the tube 12 to removably engage the tube 12 to the adapter 34. The adapter 34 shown in FIGS. 3-7 is directed to use with a tongue retractor 32, but the present invention anticipates a variety of adapters 34 for use with a multitude of medical instruments 30.

In yet another embodiment, a second fiberoptic cable 44 is engaged to the tube 12 and terminates proximate to the first terminus 24 of the tube 12. The second fiberoptic cable 44 is configured to be operationally engaged to a visible light emitter (not shown) so that visible light is emitted proximate to the first terminus 24 of the tube 12. The second fiberoptic cable 44 is configured to direct the visible light so that the visible light illuminates the tissue proximate to the first terminus 24 of the tube 12. The visible light emitter comprises a light emitting diode (not shown).

In still yet embodiment, as shown in FIG. 8, a first connector 46 is engaged to the second end 26 of the first fiberoptic cable 18. The first connector 46 is configured to selectively engage a second connector 48. The second connector 48 is operationally engaged to the ultraviolet C light emitter. The first connector 46 is positioned to selectively engage the second connector 48 to optically engage the first fiberoptic cable 18 to the ultraviolet C light emitter. Also, in this embodiment, engagement of the first connector 46 to the second connector 48 may optically engage the second fiberoptic cable 44 to the visible light emitter.

In use, the tube 12 draws in air from the immediate vicinity of the medical instrument 30. The air carries into the tube 12 fluids, droplets, particles, and aerosols that may contain pathogens. The second fiberoptic cable 44 directs the visible light onto the tissue proximate to the first terminus 24 of the tube 12 and aids in the medical procedure. The first fiberoptic cable 18 directs the ultraviolet C light from the ultraviolet C light emitter to impinge upon the tissue and pathogens proximate to the first terminus 24 of the tube 12 to inactivate the pathogens.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A far ultraviolet light application device comprising:
a tube configured to be utilized in a medical procedure;
a first fiberoptic cable engaged to a wall of the tube, the first fiberoptic cable having a first end positioned proximate to a first terminus of the tube, the first fiberoptic cable having a second end configured for operationally engaging an ultraviolet C light emitter, such that ultraviolet C light is emitted proximate to the first terminus of the tube, wherein the first fiberoptic cable is configured for directing the ultraviolet C light from the ultraviolet C light emitter such that the ultraviolet C light impinges upon tissue and pathogens proximate to the first terminus of the tube, for inactivating the pathogens; and
an adapter selectively engageable to the tube and being configured for selectively engaging a medical instrument, such that the tube is removably engaged to the medical instrument, wherein the adapter comprises:
a plate shaped complementarily to a portion of the medical instrument;
a set of clips engaged to the plate and being configured for engaging the medical instrument, such that the adapter is removably engaged to the medical instrument with the plate overlying the portion of the medical instrument; and
a receptacle engaged to the plate, the receptacle being complementary to the tube, such that the receptacle is positioned for insertion of the tube for removably engaging the tube to the adapter.

2. The far ultraviolet light application device of claim 1, wherein the tube is configured for suctioning.

3. The far ultraviolet light application device of claim 1, wherein the ultraviolet C light emitter emits at 222 nanometers, such that the ultraviolet C light is nondamaging to mammalian tissue.

4. The far ultraviolet light application device of claim 1, further including a second fiberoptic cable engaged to the tube and terminating proximate to the first terminus of the tube, the second fiberoptic cable being configured for operationally engaging a visible light emitter, such that visible light is emitted proximate to the first terminus of the tube, wherein the second fiberoptic cable is configured for directing the visible light such that the visible light illuminates the tissue proximate to the first terminus of the tube.

5. The far ultraviolet light application device of claim 4, wherein the visible light emitter comprises a light emitting diode.

6. The far ultraviolet light application device of claim 1, further including a first connector engaged to a second end of the first fiberoptic cable and being configured for selectively engaging a second connector, the second connector being operationally engaged to the ultraviolet C light emitter, such that the first connector is positioned for selectively engaging the second connector for optically engaging the first fiberoptic cable to the ultraviolet C light emitter.

7. The far ultraviolet light application device of claim 4, further including a first connector engaged to a second end of the first fiberoptic cable and being configured for selectively engaging a second connector, the second connector being operationally engaged to the ultraviolet C light emitter and the visible light emitter, such that the first connector is positioned for selectively engaging the second connector for optically engaging the first fiberoptic cable to the ultraviolet C light emitter and the second fiberoptic cable to the visible light emitter.

8. A far ultraviolet light application device comprising:
   a tube configured to be utilized in a medical procedure, the tube being configured for suctioning;
   a first fiberoptic cable engaged to a wall of the tube, the first fiberoptic cable having a first end positioned proximate to a first terminus of the tube, the first fiberoptic cable having a second end configured for operationally engaging an ultraviolet C light emitter, such that ultraviolet C light is emitted proximate to the first terminus of the tube, wherein the first fiberoptic cable is configured for directing the ultraviolet C light from the ultraviolet C light emitter such that the ultraviolet C light impinges upon tissue and pathogens proximate to the first terminus of the tube, for inactivating the pathogens, the ultraviolet C light emitter emitting at 222 nanometers, such that the ultraviolet C light is nondamaging to mammalian tissue;
   a second fiberoptic cable engaged to the tube and terminating proximate to the first terminus of the tube, the second fiberoptic cable being configured for operationally engaging a visible light emitter, such that visible light is emitted proximate to the first terminus of the tube, wherein the second fiberoptic cable is configured for directing the visible light such that the visible light illuminates the tissue proximate to the first terminus of the tube, the visible light emitter comprising a light emitting diode; and
   an adapter selectively engageable to the tube and being configured for selectively engaging a medical instrument, such that the tube is removably engaged to the medical instrument, the medical instrument comprising an examination instrument, a surgical instrument, a dental instrument, or a veterinary instrument, the adapter comprising:
      a plate shaped complementarily to a portion of the medical instrument,
      a set of clips engaged to the plate and being configured for engaging the medical instrument, such that the adapter is removably engaged to the medical instrument with the plate overlying the portion of the medical instrument, and
      a receptacle engaged to the plate, the receptacle being complementary to the tube, such that the receptacle is positioned for insertion of the tube for removably engaging the tube to the adapter.

\* \* \* \* \*